United States Patent
Yamashita

(10) Patent No.: US 11,252,342 B2
(45) Date of Patent: Feb. 15, 2022

(54) RADIATION IMAGING SYSTEM AND METHOD OF CONTROLLING RADIATION IMAGING SYSTEM

(71) Applicant: CANON KABUSHIKI KAISHA, Tokyo (JP)

(72) Inventor: Hironori Yamashita, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 171 days.

(21) Appl. No.: 16/808,921

(22) Filed: Mar. 4, 2020

(65) Prior Publication Data
US 2020/0296303 A1   Sep. 17, 2020

(30) Foreign Application Priority Data

Mar. 12, 2019   (JP) .............................. JP2019-045135

(51) Int. Cl.
*H04N 5/32*     (2006.01)
*G01T 1/164*    (2006.01)
*G01T 1/17*     (2006.01)

(52) U.S. Cl.
CPC .............. *H04N 5/32* (2013.01); *G01T 1/1645* (2013.01); *G01T 1/17* (2013.01)

(58) Field of Classification Search
CPC ........... H04N 5/32; G01T 1/1645; G01T 1/17; A61B 6/566; A61B 6/465; A61B 6/548; A61B 6/464; A61B 6/54; G06F 9/526
USPC .................................................. 250/370.09
See application file for complete search history.

(56) References Cited

U.S. PATENT DOCUMENTS

| | | | |
|---|---|---|---|
| 2005/0046642 A1 | 3/2005 | Takekoshi |
| 2010/0111257 A1 | 5/2010 | Takekoshi |
| 2011/0026676 A1 | 2/2011 | Takekoshi |
| 2012/0288064 A1 | 11/2012 | Takekoshi |
| 2016/0364484 A1 | 12/2016 | Dong |
| 2017/0251989 A1 | 9/2017 | Nishi |
| 2018/0368797 A1 | 12/2018 | Kuwata et al. |
| 2019/0098074 A1 | 3/2019 | He |
| 2019/0231297 A1 | 8/2019 | Takekoshi |
| 2020/0296159 A1 | 9/2020 | Takekoshi |

FOREIGN PATENT DOCUMENTS

| | | |
|---|---|---|
| JP | 2014-211764 | 11/2014 |
| JP | 6195348 | 9/2017 |

OTHER PUBLICATIONS

U.S. Appl. No. 16/810,138, filed Mar. 5, 2020, Koji Takekoshi.

*Primary Examiner* — David P Porta
*Assistant Examiner* — Gisselle M Gutierrez
(74) *Attorney, Agent, or Firm* — Venable LLP

(57) ABSTRACT

A radiation imaging system that is capable of controlling a radiation generating apparatus and a radiation detector based on communication between a first control application and a second control application is provided. The radiation imaging system comprises a holding unit configured to hold a plurality of processing requests transmitted from the second control application, a determination unit configured to determine whether the plurality of processing requests held in the holding unit are processing requests to be continuously executed, and a control right obtaining unit configured to obtain a control right to control an imaging control unit of the first control application that performs the control in order to continuously process the processing requests.

24 Claims, 6 Drawing Sheets

RADIATION IMAGING SYSTEM AND METHOD OF CONTROLLING RADIATION IMAGING SYSTEM

BACKGROUND OF THE INVENTION

Field of the Invention

The present invention relates to a radiation imaging system and a method of controlling the radiation imaging system and, more particularly, to a technique for causing an application for controlling radiation imaging and another application to operate in cooperation with each other.

Description of the Related Art

In recent years, the digitization of radiation imaging systems has led to the proliferation of systems designed to irradiate a radiation imaging apparatus with radiation from a radiation source through an object, make the radiation imaging apparatus generate a digital radiation image, and allow to check the image immediately after imaging. In addition, advances in network link technology have enabled pieces of software in different apparatuses to operate in cooperation with each other.

Japanese Patent No. 6195348 discloses an invention designed to prevent collision between operations when a plurality of user terminals are simultaneously operated in a medical system and a medical apparatus including one operation terminal and a plurality of user terminals that operate while communicating with each other, by using a known remote desktop mechanism called Splashtop Touchpad. According to the invention disclosed in Japanese Patent No. 6195348, priorities are assigned to operations depending on operators, operating places, and the roles of operators.

The medical system disclosed in Japanese Patent No. 6195348 is based on the premise of using remote desktops, and cannot enable cooperation of processes between applications having different GUIs, processes between applications operating on different OSs (Operating Systems), that is, processes between a plurality of applications.

In a system in which a plurality of applications operate in cooperation with each other, when a plurality of processes are to be continuously executed, it is necessary to avoid collision between processes performed by the respective applications.

The present invention provides a technique that can avoid collision between processes performed by a plurality of applications in a system in which the respective applications execute processing in cooperation with each other.

SUMMARY OF THE INVENTION

According to one aspect of the present invention, there is provided a radiation imaging system that is capable of controlling a radiation generating apparatus and a radiation detector based on communication between a first control application and a second control application, the system comprising: a holding unit configured to hold a plurality of processing requests transmitted from the second control application; a determination unit configured to determine, based on at least one of time information of the processing requests and contents of the processing requests, whether the plurality of processing requests held in the holding unit are processing requests to be continuously executed; and a control right obtaining unit configured to obtain a control right to control an imaging control unit of the first control application that performs the control in order to continuously process the processing requests if the determination unit determines that the processing requests are processing requests to be continuously executed.

According to another aspect of the present invention, there is provided a method of controlling a radiation imaging system that is capable of controlling a radiation generating apparatus and a radiation detector based on communication between a first control application and a second control application, the method comprising: holding a plurality of processing requests transmitted from the second control application in a holding unit; determining, based on at least one of time information of the processing requests and contents of the processing requests, whether the plurality of processing requests held in the holding unit are processing requests to be continuously executed; and obtaining a control right to control an imaging control unit of the first control application that performs the control in order to continuously process the processing requests if it is determined in the determining that the processing requests are processing requests to be continuously executed.

According to the present invention, it is possible to avoid collision between processes performed by a plurality of applications in a system in which the respective applications execute processing in cooperation with each other.

Further features of the present invention will become apparent from the following description of exemplary embodiments (with reference to the attached drawings).

DESCRIPTION OF THE EMBODIMENTS

Figure 1:
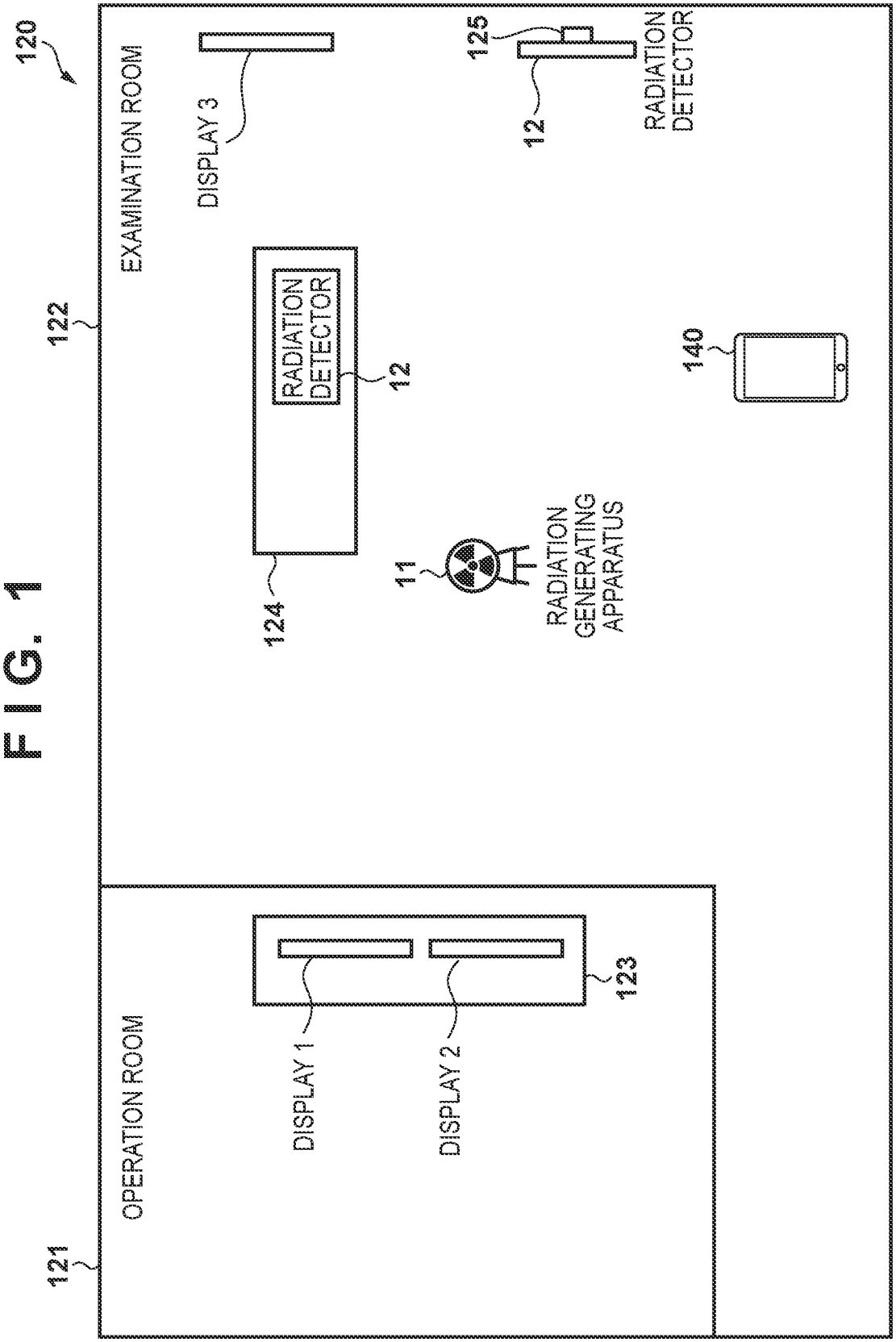
FIG. 1 is a view showing an example of the schematic arrangement of a radiation imaging system according to the first embodiment.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

First Embodiment (Example of Schematic Arrangement of Radiation Imaging System)

FIG. 1 shows an example of the schematic arrangement of a radiation imaging system according to the first embodiment. In many hospitals, a radiation imaging room 120 is divided into an operation room 121 and an examination room 122. On the operation room 121 side, mainly a radiation imaging technician (to be also referred to as an operator hereinafter) operates a control device 123 on a console. The control device 123 then controls a radiation generating apparatus 11 and radiation detectors 12 on the examination room 122 side to obtain a radiation image. The control device 123 can also perform communication and display control for displaying information concerning imaging on displays 1 to 3 and a portable terminal 140 (to be described later).

FIG. 1 shows a case in which the radiation detector 12 is installed on a supine position table 124, and the radiation detector 12 is installed on a standing position stand 125. However, the radiation imaging room 120 in FIG. 1 is merely an example and not limited to this arrangement.

The displays 1 and 2 in the operation room 121 display, for example, information for controlling the radiation imaging system to allow the operator to perform radiation imaging. In addition, the display 3 in the examination room 122 displays, for example, information for assisting imaging, such as subject information. The display 3 can also display information different from that displayed on the display 1 or 2 or display a screen as a clone of information displayed on the display 1 or 2.

Note that in this case, the single display 3 is provided but a plurality of displays may be provided in the examination room 122. In addition, as long as information can be presented to the operator, it is not always necessary to use an arrangement including displays.

The portable terminal 140 is mainly used by the operator to provide the operator with information as auxiliary information. The portable terminal 140 can also display, for example, information different from that displayed on the display device 1 or 2 or display a screen as a clone of information displayed on the display 1 or 2. In addition, the screen of the portable terminal 140 can display a screen similar to that displayed on the display 3. Although FIG. 1 shows a case in which the single portable terminal 140 is used, a plurality of portable terminals may be used. As long as information can be provided for the operator, it is also possible to use a wearable terminal or the like.

(Procedure for Examination)

A general procedure for an examination will be described next. First of all, the operator receives an order for radiation imaging via an in-hospital network. The imaging order is received in the control device 123 and specifies subject information and the contents of imaging. In general, when an imaging order is delivered to the operator, a subject waits for imaging outside the examination room 122. The operator calls the subject into the examination room 122 and prepares for an examination in accordance with the imaging order. Upon calling the subject into the examination room 122, the operator checks the name and birth date of the subject to prevent a mix-up between subjects. At this time, for example, the operator makes a check by matching the subject name on the imaging order received as subject information with information displayed on the display 3 in the examination room 122 or with the information displayed on the screen of the portable terminal 140.

Upon preparation for imaging, for example, the positions of a radiation generating apparatus 11, the subject, and the radiation detector 12 are adjusted in accordance with an imaging order for imaging at a supine position or standing position as the posture of the subject at the time of imaging. It is possible to change the order of imaging or switch the posture of the subject at the time of imaging between a supine position and a standing position in accordance with the state of the subject, the contents of an imaging order, or at operator's discretion.

Subsequently, upon moving from the examination room 122 to the operation room 121 and determining that radiation imaging can be performed, the operator inputs an instruction to start imaging to an operation unit (not shown). The control device 123 controls the radiation generating apparatus 11 and the radiation detector 12 based on the operation of the operation unit to cause the radiation generating apparatus 11 to apply radiation and the radiation detector 12 to detect radiation transmitted through a subject. The radiation detector 12 includes a pixel array in which a plurality of pixels for converting radiation into electrical signals are arranged in a matrix pattern, and can generate a radiation image corresponding to the converted electrical signals.

The control device 123 is configured to be communicable with the radiation detector 12, and obtains the radiation image generated by the radiation detector 12 by communication. The control device 123 performs display control to display the obtained radiation image on the display. Upon checking the radiation image displayed on the display and finding no problem, the operator moves to the examination room 122 to set a next imaging position, and performs imaging in the same procedure. If there is no need to perform next imaging, the examination is terminated, and the subject leaves the imaging room.

(Functional Arrangement of Radiation Imaging System)

Figure 2:
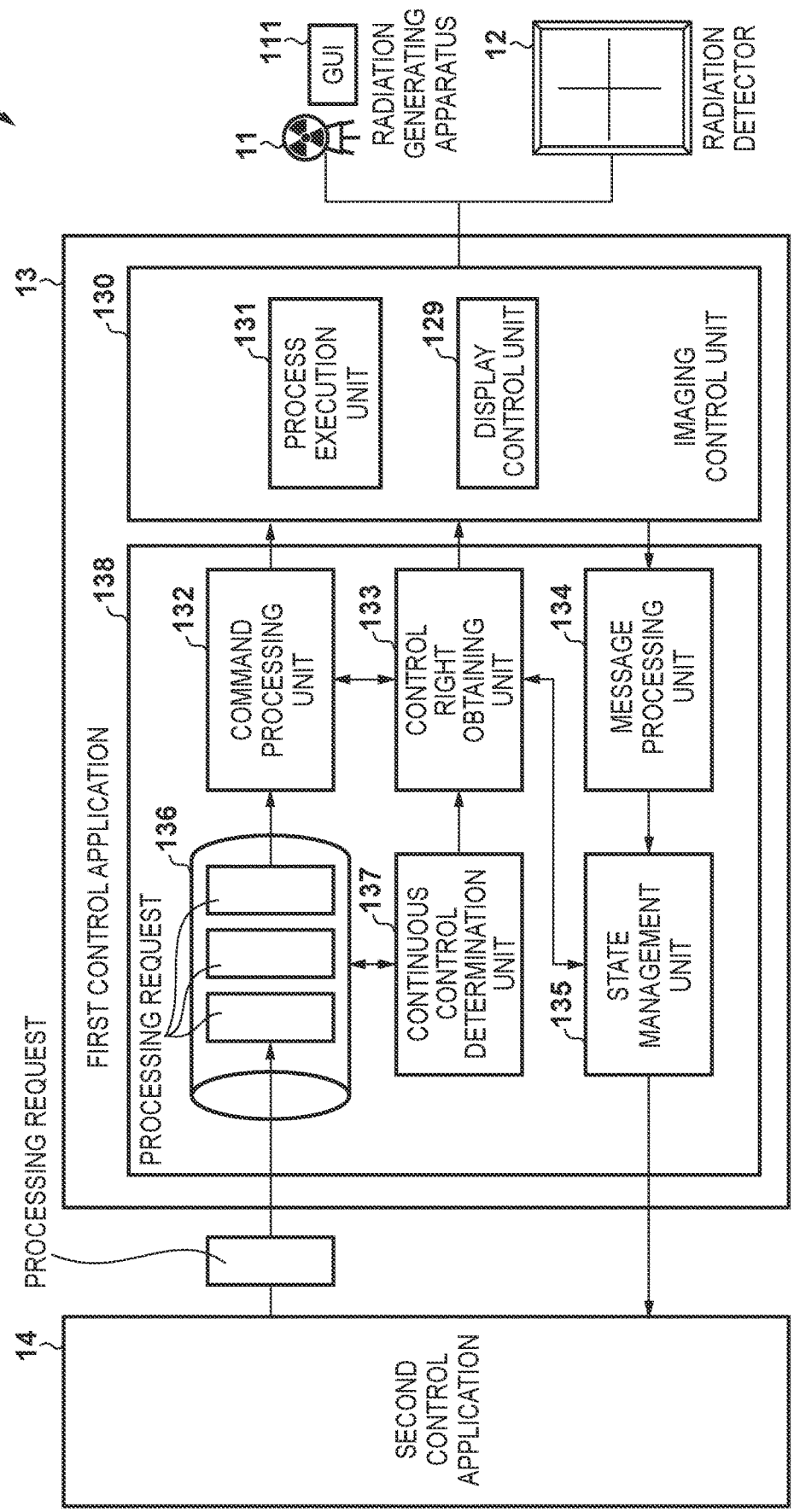
FIG. 2 is a block diagram exemplarily showing the functional arrangement of the radiation imaging system according to the first embodiment.

The functional arrangement of a radiation imaging system 10 will be described next with reference to FIG. 2. The radiation imaging system 10 includes the radiation generating apparatus 11 that generates radiation, the radiation detector 12 that detects radiation, and the control device 123 (computer) that controls the radiation generating apparatus 11 and the radiation detector 12. The radiation imaging system 10 is capable of controlling the radiation generating apparatus 11 and the radiation detector 12 based on communication between the first control application 13 and the second control application 14. The first control application 13 is, for example, an application operating on the control device 123 (computer). Processing by each unit constituting the first control application 13 is implemented as a functional component of the control device 123 (to be also referred to as the first control device).

The second control application 14 may be an application operating on the same computer on which the first control application 13 operates or an application operating on a computer (for example, the portable terminal 140) different from the control device 123 (computer) on which the first control application 13 operates. In addition, the second control application 14 need not be a single application and may include a plurality of applications providing different GUIs.

The functional arrangement of the first control application 13 will be described next. An imaging control unit 130 (main logic unit) includes a display control unit 129 that provides a GUI (Graphical User Interface) and controls the display of the GUI and a process execution unit 131 that executes imaging control in the radiation imaging system 10. The imaging control unit 130 can singly operate. The imaging control unit 130 controls the radiation imaging system 10 while making the radiation generating apparatus 11 and the radiation detector 12 cooperate with each other.

For example, operations instructed from the GUIs displayed on the displays 1 and 2 are input to the process execution unit 131. The process execution unit 131 processes the operations. In the imaging control unit 130, the process execution unit 131 can execute various processes such as processing instructions from a GUI 111 of the radiation generating apparatus 11, processing instructions from the radiation detector 12, and processing instructions notified from the computer.

A dynamic link library (to be referred to as a DLL 138 (communication control unit) hereinafter) operates as a plugin of the imaging control unit 130. The imaging control unit 130 having a plugin structure can singly operate and can also operate in cooperation with the DLL 138. The imaging control unit 130 need not always have a plugin structure and may be configured to operate in cooperation with the DLL 138. This embodiment will exemplify a case in which the DLL 138 has a plugin structure.

The internal structure of the DLL 138 is roughly divided into two types of processing units. That is, the DLL 138 includes a command processing unit 132 that processes processing requests from the second control application 14 and a message processing unit 134 that processes processing requests from the imaging control unit 130 of the first control application 13. A processing request from the second control application 14 is called a command. A processing request from the imaging control unit 130 of the first control application 13 is called a message.

In this case, the second control application 14 may be an application that operates on the same control device 123 (computer) as that on which the first control application 13 operates or an application that operates on a control device (to be also referred to as the second control device) different from the control device 123 (computer).

A command processing request is held in a processing queue 136 (holding unit) that can receive a plurality of processing requests from the second control application 14. The processing queue 136 (holding unit) can hold the processing requests transmitted from the second control application 14 in the transmission order. The command processing unit 132 notifies the imaging control unit 130 of the processing request held in the processing queue 136. When the command processing unit 132 notifies the imaging control unit 130 of the command processing request, a control right obtaining unit 133 obtains a control right on the imaging control unit 130. The control right can obtain a main thread or GUI thread from the imaging control unit 130 by using exclusive processing such as mutex or semaphore. According to C #language, it is possible to obtain a control right by using known Dispatcher.Invoke as a GUI thread.

Note, however, that when a control right is obtained and released for each command (each command processing request) processed by the command processing unit 132, a state without a control right (a period without a control right) can occur between processing requests from the second control application 14. For this reason, when processing based on a processing request (message) on the first control application side is executed during a period without a control right, subsequent processing based on a processing request (command) on the second control application side may not be executed as intended by the user.

Upon determining, based on the contents and the like of the processing requests held in the processing queue 136, that there is a processing request to be continuously executed, a continuous control determination unit 137 instructs the control right obtaining unit 133 to continuously obtain a control right even in the period between processing requests. That is, the continuous control determination unit 137 issues an instruction to hold a control right obtained by the control right obtaining unit 133 even in the period between processing requests (the period between a command processing request and a subsequent command processing request). In this case, a command processing request to be continuously executed is a series of operations with respect to the first control application 13. A specific example of this processing will be described later with reference to the case shown in FIG. 6. If the continuous control determination unit 137 determines that there is a processing request to be continuously executed, the control right obtaining unit 133 obtains a control right on the imaging control unit 130 of the first control application to continuously execute the processing of the processing request.

In message processing, when the state of the first control application 13 has changed upon processing by the process execution unit 131 in accordance with a given processing request from the first control application 13, the imaging control unit 130 notifies the message processing unit 134 of the DLL 138 of a message stating that the state of the first control application 13 has changed. When the message processing unit 134 has received the message from the imaging control unit 130 and the state of the imaging control unit 130 has changed, the message processing unit 134 changes the state information managed by a state management unit 135.

(Example of Cooperative Operation in Radiation Imaging System)

Figure 6:
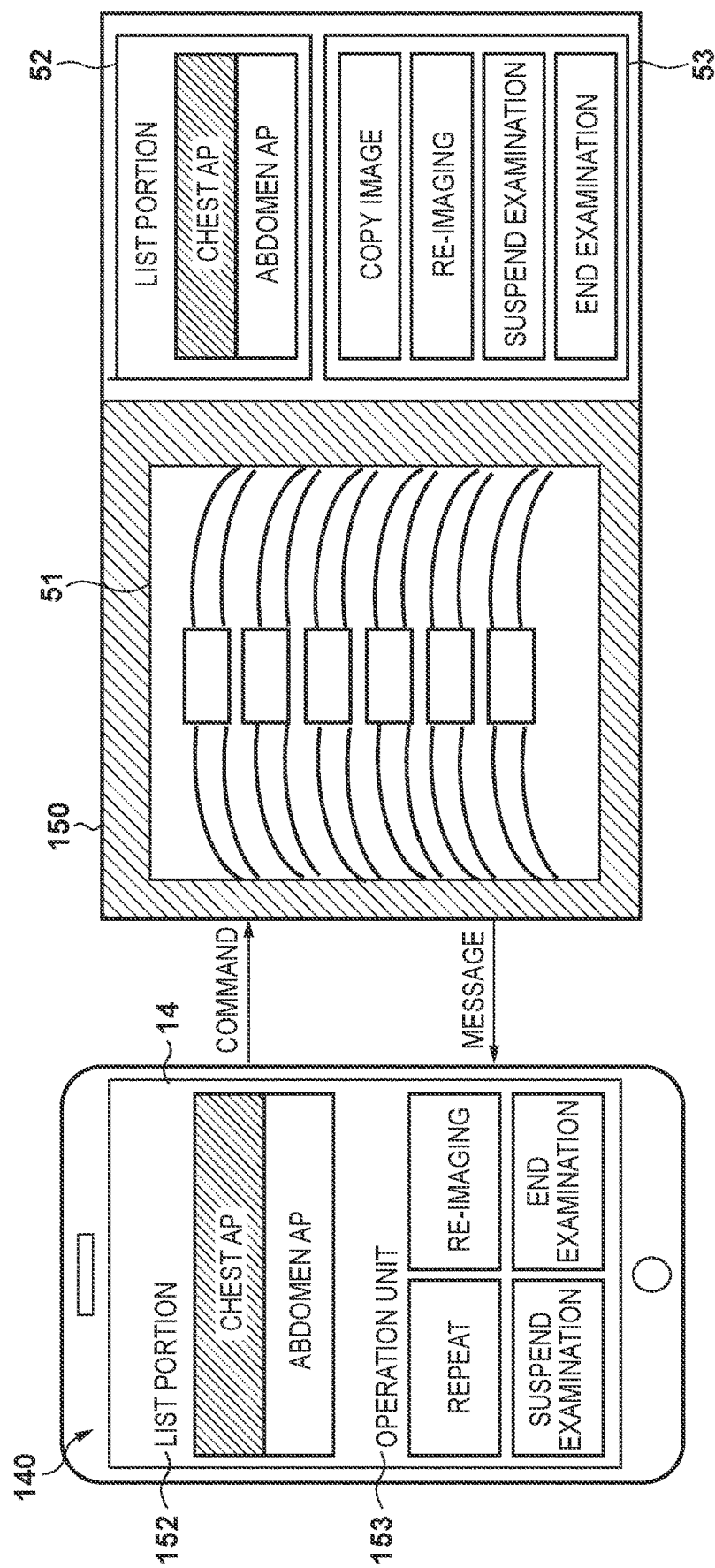
FIG. 6 is a view for explaining an example of a cooperative operation in the radiation imaging system.

An example of a cooperative operation in the radiation imaging system 10 will be described next. FIG. 6 is a view for explaining an example of a cooperative operation in the radiation imaging system 10. Note that the description made with reference to FIG. 6 is merely an example, and does not limit this embodiment.

The operator carries the portable terminal 140. The display control unit 129 of the first control application 13 can perform display control to display various GUIs on both or either of the displays 1 and 2. Assume that in this case, an imaging screen displaying the radiation image obtained from the radiation detector 12 is displayed on a GUI 150 displayed by the display control unit 129 of the first control application 13.

FIG. 6 shows the representation of a GUI on the display 1 or 2 as the first control application 13, and the representation of a GUI on the portable terminal 140 as the second control application 14 in order to exemplarily describe cooperation between the first control application 13 and the second control application 14 in the portable terminal 140.

Assume that the imaging screen displays a radiation image display area 51 that displays an obtained radiation image, an obtained image list portion 52 that displays a list of obtained radiation images, and an operation portion 53 for executing various types of processes (for example, image copying, re-imaging, examination suspension, and a termination operation) with respect to an obtained image.

In this imaging screen, when a radiation image is displayed, the first control application 13 transmits a message for notifying the portable terminal 140 of information indicating that the radiation image is displayed on the imaging screen. The portable terminal 140 to which the message is transmitted from the first control application 13 can recognize from the contents of the message that the radiation image is displayed. In accordance with this state, the portable terminal 140 can also freely display a screen on the GUI of the portable terminal 140 under the display control of the second control application 14.

Assume, for the sake of simplicity, that like the first control application 13, the portable terminal 140 displays an operation screen for an obtained image which is dedicated to the portable terminal 140. However, this screen display is an example, and a different screen may be displayed. In this case, the operator may either operate on the obtained image displayed based on display control of the first control application 13 or operate on the obtained image displayed based on display control of the second control application 14 of the portable terminal 140.

When an operation to issue an instruction to perform re-imaging is designated from the operation portion 53 displayed on the first control application 13, the process execution unit 131 controls the radiation generating apparatus 11 and the radiation detector 12 to execute re-imaging processing. At this time, the first control application 13 transmits the result of success or failure of re-imaging processing as a message to the second control application 14 of the portable terminal 140. If, for example, re-imaging has succeeded, the first control application 13 transmits image information for specifying a re-imaging target image and operation information indicating the execution of the re-imaging operation to the second control application 14 of the portable terminal 140. The GUI of the portable terminal 140 performs highlighting so as to explicitly indicate the execution of re-imaging of a chest region (chest AP) under the display control of the second control application 14. This makes it possible to also display a GUI screen corresponding to the result of re-imaging processing on the portable terminal 140.

When the portable terminal 140 has issued a re-imaging instruction, the second control application 14 of the portable terminal 140 transmits a command including image information for specifying a re-imaging target image and operation information indicating the execution of a re-imaging operation to the first control application 13. Upon receiving the command from the second control application 14, the process execution unit 131 of the first control application 13 selects a re-imaging target image from the obtained image list portion 52 and executes a series of processes up to a re-imaging operation on the operation portion 53 as in the case in which the first control application 13 has issued an instruction to perform a re-imaging operation.

The first control application 13 transmits the result of success or failure of re-imaging processing as a message to the second control application 14 of the portable terminal 140. In this case, information similar to that in the case of issuing a re-imaging instruction on the first control application 13 side is transmitted to the second control application 14 of the portable terminal 140.

If, for example, re-imaging has succeeded, a message including image information for specifying a re-imaging target image and operation information indicating the execution of a re-imaging operation is transmitted to the second control application 14 of the portable terminal 140. The GUI of the portable terminal 140 performs highlighting to explicitly indicate the execution of re-imaging of the chest region (chest AP) under the display control of the second control application 14. This makes it possible to display a GUI screen corresponding to the result of re-imaging processing on the portable terminal 140 side.

As in the case described with reference to FIG. 6, when issuing operation instructions from the portable terminal 140, the operator sometimes continuously executes a plurality of commands by selecting a re-imaging target image with an obtained image list portion 152 and selecting a re-imaging operation with an operation portion 153. For example, the operator generates a processing request (command) concerning a re-imaging target image by a selective operation on the list portion 152 and further generates a processing request (command) concerning the selection of a re-imaging operation by a selective operation on the operation portion 153. The second control application 14 transmits the generated processing requests (commands) to the first control application 13. In this case, the processing queue 136 holds the two processing requests (commands) transmitted from the second control application 14. Note that the processing requests (commands) generated by the second control application are not limited to the above two examples. A plurality of processing requests (commands) are generated in accordance with various operations input from the GUI of the portable terminal 140.

The continuous control determination unit 137 can determine whether to continuously execute a plurality of processing requests (commands) held in the processing queue 136 based on the contents of each processing request and time information concerning each processing request. The continuous control determination unit 137 may perform this determination based on at least the contents of each processing request and the time information concerning each processing request or based on both the contents of each processing request or the time information concerning each processing request. For example, a determination method based on the notification time of each processing request, as time information, can determine, by referring to the time when the second control application 14 has notified the first control application 13 of each processing request, that processing requests at the same notification time or the processing request notified first and the processing request notified within a predetermined period since the first notification time are the processing requests notified at the same time. Note that as a notification time, the time information corresponding to each processing request (command) held in the processing queue 136 can be used. Alternatively, time information corresponding to each processing request (command) generated by the second control application 14 can be used.

If the processing contents of processing requests held in the processing queue 136 correspond to processing requests (for example, operation requests on the list portion 152 and the operation portion 153 in FIG. 6) within the same screen on the GUI provided by the first control application, the continuous control determination unit 137 can determine that the processing request should be continuously executed. In addition, if a plurality of processing requests correspond to a series of operations on the GUI, the continuous control determination unit 137 can determine that the processing requests should be continuously executed.

When there are a plurality of processing requests to be continuously executed, the continuous control determination unit 137 instructs the control right obtaining unit 133 to also maintain the state in which a control right is obtained in the period between processing requests. The control right obtaining unit 133 keeps holding the control right on the imaging control unit 130 until processing requests for the selection of an obtained image and the execution of a re-imaging operation are notified to the command processing unit 132 and the plurality of processing requests are completely processed based on the determination result obtained by the continuous control determination unit 137. That is, the control right obtaining unit 133 holds the control right on the imaging control unit 130 in the period from the start of the processing of a processing request concerning the selection of an obtained image to the end of the processing of a processing request concerning the execution of a subsequent re-imaging operation based on the determination result obtained by the continuous control determination unit 137.

(Procedure of Processing in Continuous Execution of Plurality of Commands)

Figure 3:
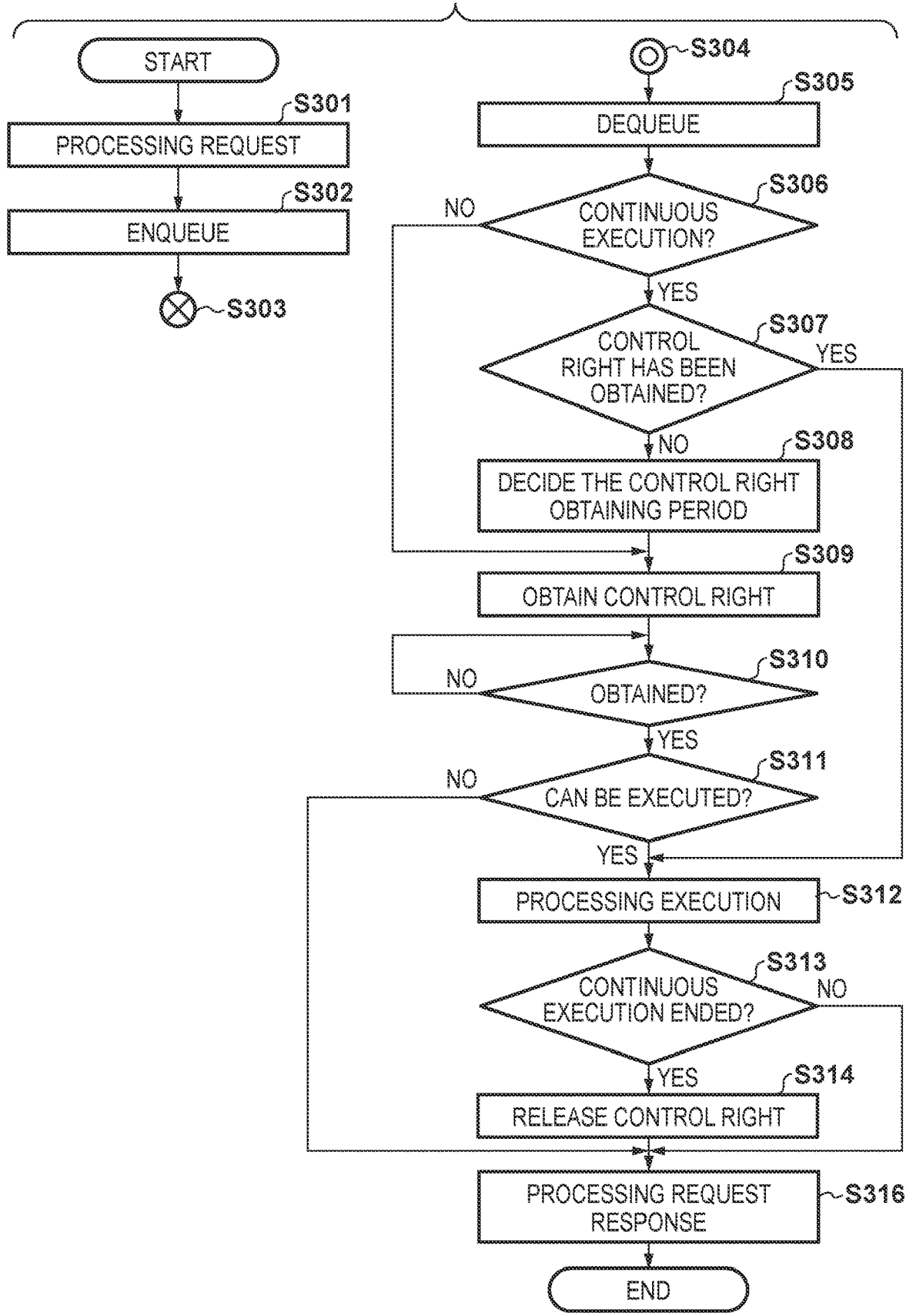
FIG. 3 is a flowchart showing a procedure of processing in the system according to the first embodiment.

Processing by the first control application 13 in a case in which a plurality of processing requests (commands) are continuously executed will be described next with reference to the flowchart of FIG. 3.

In step S301, the second control application 14 notifies the first control application 13 of a processing request (command). The DLL 138 is formed into an API (Application Programing Interface). The second control application 14 can notify a processing request (command) by invoking the API of the DLL 138.

In step S302, the processing queue 136 holds (enqueues) the processing request (command) notified from the second control application 14 in step S301. When the processing request (command) is enqueued, the queueing procedure is temporarily terminated in step S303. The process then advances to step S304.

In step S304, when the processing request (command) held in the processing queue 136 can be processed, the process advances to step S305. In step S305, the command processing unit 132 obtains (dequeues) the queued processing request from the processing queue 136. The command processing unit 132 obtains processing requests (commands) from the processing queue 136 according to the FIFO (First In First Out) principle.

In step S306, the continuous control determination unit 137 determines whether the plurality of processing requests (commands) obtained from the processing queue 136 should be continuously executed. The continuous control determination unit 137 refers to time information (for example, notification times) of the processing requests enqueued in the processing queue 136 to determine whether the processing requests should be continuously executed. The continuous control determination unit 137 refers to the notification times as time information when the second control application 14 has notified the first control application 13 of the processing requests to determine that processing requests at the same notification time or the processing request notified first and the processing request notified within a predetermined period since the first notification time are the processing requests notified at the same time. The continuous control determination unit 137 determines that the processing requests notified at the same time are processing requests to be continuously executed.

Upon determining in step S306 that the processing requests should not be continuously executed (NO in step S306), the continuous control determination unit 137 advances the process to step S309. In contrast to this, upon determining in step S306 that the processing requests should be continuously executed (YES in step S306), the continuous control determination unit 137 advances the process to step S307.

In step S307, in order to process the processing requests (commands), the control right obtaining unit 133 determines whether a control right on the imaging control unit 130 has been obtained. If a control right has been obtained (YES in step S307), the process advances to step S312. Upon determining in step S307 that a control right on the imaging control unit 130 has not been obtained (NO in step S307), the control right obtaining unit 133 advances the process to step S308.

In step S308, the control right obtaining unit 133 decides a control right obtaining period based on the determination result obtained by the continuous control determination unit 137. In this case, the control right obtaining unit 133 decides, as a control right obtaining period for a plurality of processing requests determined by the continuous control determination unit 137 as processing requests to be continuously executed, the period from the start of the first processing of a processing request to the end of the processing of the last processing request.

In step S309, the control right obtaining unit 133 obtains a control right on the imaging control unit 130. In this case, the control right can obtain a main thread or GUI thread from the imaging control unit 130 by using exclusive processing such as mutex or semaphore. According to C #language, it is possible to obtain a control right by using known Dispatcher.Invoke as a GUI thread.

In step S310, the control right obtaining unit 133 determines whether a control right on the imaging control unit 130 was able to be obtained. If a control right was not able to be obtained (NO in step S310), the control right obtaining unit 133 waits in a state of waiting for a control right until a control right on the imaging control unit 130 is released. Note that if a control right was not able to be obtained, the process may advance to step S316 to output a processing request response indicating that a control right was not able to be obtained and the processing of a processing request (command) has failed.

Upon determining in step S310 that a control right was able to be obtained (YES in step S310), the control right obtaining unit 133 advances the process to step S311.

In step S311, the control right obtaining unit 133 determines whether the current state is a state in which a processing request (command) can be executed by the obtained control right. The state management unit 135 manages the state of the imaging control unit 130. The control right obtaining unit 133 determines, based on the state of the imaging control unit 130 managed by the state management unit 135, whether the current state is a state in which a processing request (command) can be executed. This state includes, for example, a state of screen transition on the GUI 150 subjected to display control by the display control unit 129 of the imaging control unit 130 and a state in which an operation button on a screen can be operated or not. When, for example, the GUI 150 is in state shown in FIG. 6, the screen state is an imaging screen, and the re-imaging button is operative.

No screen other than the screen displayed on the GUI 150 in FIG. 6 is displayed, and hence the control right obtaining unit 133 determines that no operation other than the operations on the displayed screen is operative. Accordingly, the control right obtaining unit 133 determines that a processing request to press one of the buttons on the operation portion 53 can be executed in a state in which the GUI 150 in FIG. 6 is displayed, but a processing request to press a different button other than those cannot be executed. The determination result obtained by the control right obtaining unit 133 is notified to the command processing unit 132. If the processing request (command) can be executed, the command processing unit 132 notifies the imaging control unit 130 of the processing request (command) obtained from the processing queue 136.

Note that the processing in step S311 can be skipped with respect to processing requests (commands) that do not accompany any control operations such as the screen transition of the GUI and can be always executed regardless of the state of a screen or the state of imaging control. In general, whether each processing request can be always executed is defined for each API, and it is possible to determine in accordance with the definition whether each processing request is a command that can be executed.

In step S312, the process execution unit 131 executes the processing request (command) notified from the command processing unit 132. That is, the process execution unit 131 performs control to mimic the operation by the operator on the GUI 150 (the operation screen in FIG. 6) based on the processing request (command) based on the operation of the portable terminal 140.

In step S313, the command processing unit 132 determines, based on the determination result obtained by the continuous control determination unit 137, whether processing concerning processing requests to be continuously executed is complete. If the command processing unit 132 has notified the imaging control unit 130 of all the processing requests to be continuously executed and determines that all the processing requests have been completely processed (YES in step S313), the process advances to step S314. In step S314, the control right obtaining unit 133 releases the obtained control right.

Upon determining in step S313 that not all the continuous processing requests have been completed (NO in step S313), the command processing unit 132 advances the process to step S316 while holding the control right.

In step S316, the processing result obtained by the imaging control unit 130 is notified to the second control application 14. The message processing unit 134 receives a message concerning the execution of the processing request (command) from the imaging control unit 130. When the state of the imaging control unit 130 changes, the message processing unit 134 changes the state information managed by the state management unit 135. If the message received from the imaging control unit 130 indicates success in the processing of the processing request (command), the state management unit 135 notifies the second control application 14 of success in the processing of the processing request (command). In contrast, if the message received from the imaging control unit 130 indicates a failure in the processing of the processing request (command), the state management unit 135 notifies the second control application 14 of the failure in the processing of the processing request (command). Although there are various processing failure causes, the second control application 14 can notify a combination of information indicating processing failure causes.

Second Embodiment

The first embodiment has exemplified the arrangement configured to determine whether processing requests from the second control application 14 are processing requests to be continuously executed and to hold a control right on the imaging control unit 130 of the first control application 13 for a predetermined period based on the determination result. The second embodiment will exemplify an arrangement provided with an interrupt detection unit 139 that detects the occurrence of an interrupt operation from an imaging control unit 130 of a first control application 13.

Figure 4:
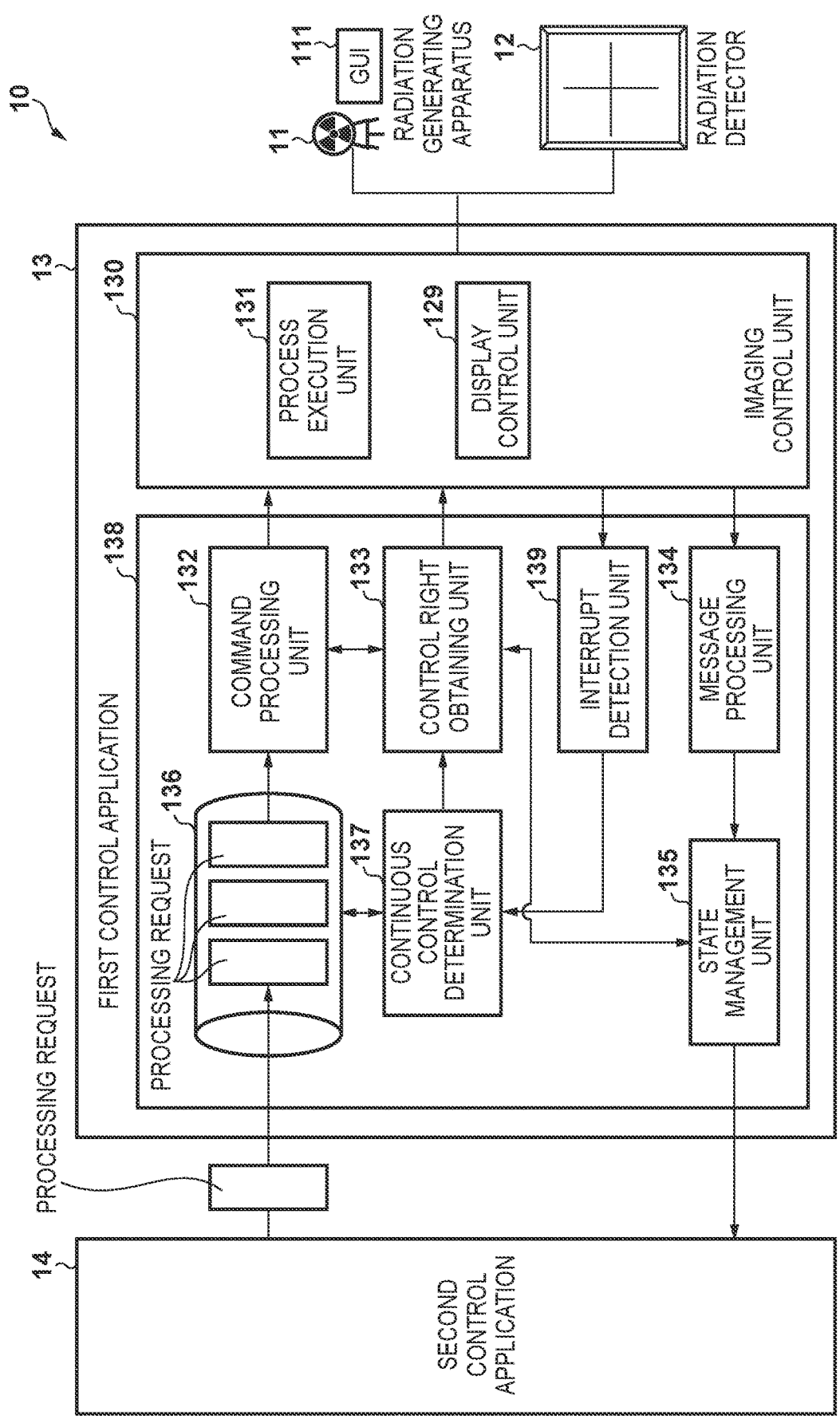
FIG. 4 is a block diagram exemplarily showing the functional arrangement of a radiation imaging system according to the second embodiment.

FIG. 4 exemplarily shows the functional arrangement of a radiation imaging system 10 according to the second embodiment. The interrupt detection unit 139 detects an interrupt operation that has occurred in the imaging control unit 130, and inputs the detection result to a continuous control determination unit 137. The continuous control determination unit 137 determines whether it is possible to perform an interrupt operation during the execution of a processing request (command).

Figure 5:
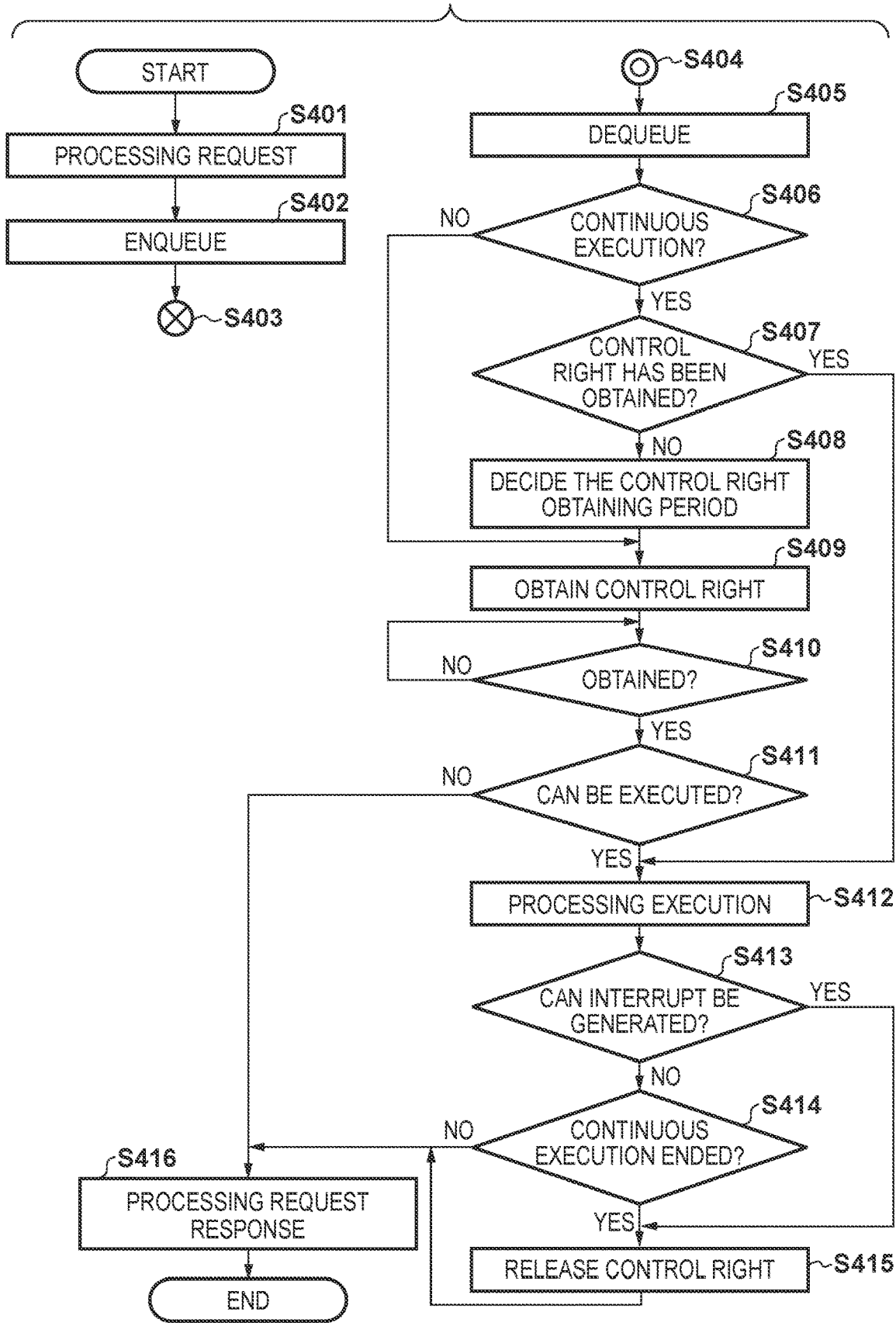
FIG. 5 is a flowchart showing a procedure of processing in the system according to the second embodiment.

FIG. 5 is a flowchart showing a procedure of processing in the system according to the second embodiment. Processing in steps S401 to S412 is the same as the processing in steps S301 to S312 in FIG. 3, which has been described in the first embodiment.

In step S413, the interrupt detection unit 139 detects an interrupt when an operation is performed on the first control application 13 side. The interrupt detection unit 139 inputs the operation interrupt detection result to the continuous control determination unit 137. The continuous control determination unit 137 determines whether an interrupt can be generated during the execution of a processing request (command). If the processing contents of a processing request (command) held in the processing queue 136 and planned to be obtained (dequeued) next correspond to a processing request accompanying screen transition of the GUI, the continuous control determination unit 137 determines that an interrupt can be generated for the processing request (interrupt processing) from the first control application 13. That is, the continuous control determination unit 137 determines that a processing request (interrupt processing) from the first control application 13 can be preferentially processed with respect to the processing of processing requests (commands) held in the processing queue 136.

Note that the continuous control determination unit 137 determines in step S413 whether an interrupt can be generated, based on whether the processing request is a processing request accompanying screen transition of the GUI. However, this is not exhaustive. For example, this system may be provided with a setting unit that sets a priority for each processing request (command) from the second control application 14 and configured to determine that an interrupt can be generated if the priority set for the processing request (command) planned to be obtained next from the processing queue 136 corresponds to a priority that allows an interrupt (for example, the priority of processing contents is low). That is, if a priority set for the processing request (command) held in the processing queue 136 and planned to be obtained next is lower than a priority set for an interrupt processing request from the first control application 13, the continuous control determination unit 137 determines that an interrupt can be generated with respect to the processing request from the first control application 13. If the continuous control determination unit 137 determines in step S413 that an interrupt cannot be generated, the second control application 14 may notify the user of information indicating that interrupt processing cannot be executed. For example, notification can be performed by displaying a message on a GUI 150 or generating a sound. The GUI 150 or a loudspeaker (not shown) functions as a notification unit.

Upon determining that an interrupt for a processing request (interrupt processing) can be generated (YES in step S413), the continuous control determination unit 137 advances the process to step S415.

In step S415, a control right obtaining unit 133 releases the obtained control right. Upon determining in step S413 that an interrupt cannot be generated (NO in step S413), the continuous control determination unit 137 advances the process to step S414.

In step S414, a command processing unit 132 determines, based on the determination result obtained by the continuous control determination unit 137, whether the processing requests to be continuously executed have been completely processed. Upon notifying the imaging control unit 130 of all the processing requests to be continuously executed and determining that all the processing requests have been completed processed (YES in step S414), the command processing unit 132 advances the process to step S415. In step S415, the control right obtaining unit 133 releases the obtained control right.

Upon determining in step S414 that not all the processing requests to be continuously executed have been completely processed (NO in step S414), the control right obtaining unit 133 maintains the held state of the control right. That is, the control right obtaining unit 133 advances the process to step S416 while holding the control right. Processing in step S416 is the same as that in step S316 in FIG. 3.

According to each embodiment described above, even when a plurality of applications execute processing in cooperation with each other, it is possible to avoid collision between processes performed by the respective applications.

That is, in the system in which a plurality of different applications simultaneously operate in corporation with each other, it is possible to solve the problem of collision when continuously performing a plurality of processes. Even if, therefore, processes are simultaneously executed, it is possible to perform the processes without collision. In addition, by deciding a period during which a control right to perform exclusive control when continuously performing a plurality of processes is obtained, it is possible to improve cumbersomeness in manual setting of a continuous processing period or responsiveness in application operations.

Other Embodiments

Embodiment(s) of the present invention can also be realized by a computer of a system or apparatus that reads out and executes computer executable instructions (e.g., one or more programs) recorded on a storage medium (which may also be referred to more fully as anon-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-045135, filed on Mar. 12, 2019, which is hereby incorporated by reference herein in its entirety.

What is claimed is:

1. A radiation imaging system that is capable of controlling a radiation generating apparatus and a radiation detector based on communication between a first control application and a second control application, the system comprising:
    a holding unit configured to hold a plurality of processing requests transmitted from the second control application;
    a determination unit configured to determine, based on at least one of time information of the processing requests and contents of the processing requests, whether the plurality of processing requests held in the holding unit are processing requests to be continuously executed; and
    a control right obtaining unit configured to obtain a control right to control an imaging control unit of the first control application that performs the control in order to continuously process the processing requests if the determination unit determines that the processing requests are processing requests to be continuously executed.

2. The system according to claim 1, wherein the determination unit refers to, as the time information, notification times when the second control application has notified the first control application of processing requests and determines processing requests notified at the same notification time as processing requests to be continuously executed.

3. The system according to claim 1, wherein the determination unit determines, based on the time information, that a processing request notified within a predetermined period since when the second control application has notified first the first control application of the processing request is a processing request notified at the same time, and determines that the processing requests notified at the same time are processing requests to be continuously executed.

4. The system according to claim 1, wherein the determination unit determines, as processing requests to be continuously executed, processing requests held in the holding unit that are present within the same screen on a GUI provided by the first control application.

5. The system according to claim 1, wherein the control obtaining unit decides an obtaining period during which the control right is held, based on a determination result obtained by the determination unit.

6. The system according to claim 5, wherein the control right obtaining unit decides, as the obtaining period of the control right, a period from a start of processing of a first processing request to an end of processing of a last processing request.

7. The system according to claim 1, wherein the control right obtaining unit determines whether the control right was able to be obtained and, if the control right was not able to be obtained, waits for obtaining a control right until the control right on the imaging control unit is released.

8. The system according to claim 7, further comprising a state management unit configured to manage a state of the imaging control unit,
    wherein the control right obtaining unit determines, based on a state of the imaging control unit managed by the state management unit, whether a processing request can be executed.

9. The system according to claim 8, wherein if the control right is obtained and it is determined that the processing requests are ready to be executed, the imaging control unit continuously processes the processing requests that are determined by the determination unit.

10. The system according to claim 1, wherein the control right obtaining unit releases the obtained control right if the processing requests determined by the determination unit are completely processed.

11. The system according to claim 1, wherein the control right obtaining unit maintains a held state of a control right if the processing requests determined by the determination unit are not completely processed.

12. The system according to claim 1, further comprising an interrupt detection unit configured to detect an interrupt when an operation is performed on the first control application,
wherein the determination unit determines, based on an interrupt detection result obtained by the interrupt detection unit, whether an interrupt can be generated during execution of the processing request.

13. The system according to claim 12, wherein the determination unit determines that an interrupt for a processing request from the first control application can be generated if processing contents of a processing request planned to be obtained next and held in the holding unit correspond to a processing request accompanying screen transition of a GUI provided by the first control application.

14. The system according to claim 12, wherein the determination unit determines that an interrupt for a processing request from the first control application can be generated if a priority set for a processing request planned to be obtained next and held in the holding unit is lower than a priority set for an interrupt processing request from the first control application.

15. The system according to claim 12, wherein the control right obtaining unit releases an obtained control right if the determination unit determines that an interrupt for a processing request from the first control application can be generated.

16. The system according to claim 12, further comprising a notification unit configured to perform notification indicating that an interrupt for a processing request from the first control application cannot be generated if the determination unit determines that the interrupt cannot be generated.

17. The system according to claim 1, wherein the holding unit holds the plurality of processing requests transmitted from the second control application in a transmission order.

18. A method of controlling a radiation imaging system that is capable of controlling a radiation generating apparatus and a radiation detector based on communication between a first control application and a second control application, the method comprising:

holding a plurality of processing requests transmitted from the second control application in a holding unit;
determining, based on at least one of time information of the processing requests and contents of the processing requests, whether the plurality of processing requests held in the holding unit are processing requests to be continuously executed; and
obtaining a control right to control an imaging control unit of the first control application that performs the control in order to continuously process the processing requests if it is determined in the determining that the processing requests are processing requests to be continuously executed.

19. The method according to claim 18, wherein in the determining, notification times when the second control application has notified the first control application of processing requests are referred to as the time information and processing requests notified at the same notification time are determined as processing requests to be continuously executed.

20. The method according to claim 18, wherein in the determining, processing requests held in the holding unit that are present within the same screen on a GUI provided by the first control application are determined as processing requests to be continuously executed.

21. The method according to claim 18, wherein in the obtaining, it is determined whether the control right was able to be obtained and, if the control right was not able to be obtained, a wait state for obtaining a control right is maintained until the control right on the imaging control unit is released.

22. The method according to claim 18, wherein a held state of a control right is maintained in the obtaining if the processing requests determined in the determining are not completely processed.

23. The method according to claim 18, further comprising detecting an interrupt when an operation is performed on the first control application,
wherein in the determining, it is determined, based on an interrupt detection result obtained in the detecting, whether an interrupt can be generated during execution of the processing request.

24. The method according to claim 23, further comprising performing notification indicating that an interrupt for a processing request from the first control application cannot be generated when it is determined in the determining that the interrupt cannot be generated.

* * * * *